(12) United States Patent
Takashina (10) Patent No.: US 6,408,200 B1
(45) Date of Patent: Jun. 18, 2002

(54) EKG RECORDING ELECTRODE DEVICE

(76) Inventor: Tsunekazu Takashina, 4-14, Fukaeminamimachi 1-chome, Higashinada-ku, Kobe-shi, Hyogo-ken (JP)

(*) Notice: Subject to any disclaimer, the term of this patent is extended or adjusted under 35 U.S.C. 154(b) by 0 days.

(21) Appl. No.: 09/633,536

(22) Filed: Aug. 7, 2000

(30) Foreign Application Priority Data

Aug. 18, 1999 (JP) .......................................... 11-231548

(51) Int. Cl.[7] .............................................. A61B 5/0408
(52) U.S. Cl. ........................ 600/382; 600/386; 600/393
(58) Field of Search ................................. 600/382, 384, 600/386, 388, 390–393; 607/149, 152, 153

(56) References Cited

U.S. PATENT DOCUMENTS

| | | | | |
|---|---|---|---|---|
| 3,612,061 A | * | 10/1971 | Collins et al. | 607/149 |
| 4,202,344 A | * | 5/1980 | Mills et al. | 600/393 |
| 4,498,480 A | * | 2/1985 | Mortensen | 600/393 |
| 4,583,549 A | * | 4/1986 | Manoli | 600/393 |
| 4,608,987 A | * | 9/1986 | Mills | 600/393 |
| 5,224,479 A | * | 7/1993 | Sekine | 600/393 |
| 5,782,238 A | * | 7/1998 | Beitler | 600/393 |

FOREIGN PATENT DOCUMENTS

| CH | 274612 | * | 7/1951 | 600/393 |
|---|---|---|---|---|

OTHER PUBLICATIONS

Barr et al, "A device for rapid ECG monitoring", Anaesthesia, vol. 27, No. 1, Jan. 1972.*
Nikkei Medical Journal, published Oct. 10, 1992.

* cited by examiner

*Primary Examiner*—Lee Cohen
(74) *Attorney, Agent, or Firm*—Jordan and Hamburg LLP (57) ABSTRACT

This invention is intended to provide an EKG recording electrode device which can be easily and quickly fitted to a patient without giving uncomfortable bodily sensations to the patient even if it is difficult to change the position of the patient, making it possible to properly take an electrocardiogram. An EKG recording electrode device comprises an electrode holder made of a sheet material having flexibility and a size suited for placing on an upper front part of a human body, and a plurality of electrodes attached to the electrode holder, each electrode including a contact portion having a curved surface on the side which comes into contact with a human skin.

20 Claims, 10 Drawing Sheets

EKG RECORDING ELECTRODE DEVICE

BACKGROUND OF THE INVENTION AND RELATED ART STATEMENT

The present invention relates to an EKG recording electrode device which is used when taking an electrocardiogram in emergency cases, on-site or at a hospital, or in ordinary diagnosis at a hospital, for example.

Conventionally, an electrocardiogram is taken with electrodes attached to the chest of a human body by a suction cup method in which the electrodes built in suction cups are attached to the body surface after pretreating it by applying jelly, for example, or by a tape method in which the electrodes are attached to by means of adhesive tape. These electrode attaching methods, however, are not suited for diagnosis of emergency cases because the time required for attaching the electrodes is long. Therefore, it makes difficult to record a standard 12-lead electrocardiogram in a short time when above electrode attaching methods are used.

The suction cup method has such additional problems that too small a negative pressure in the suction cups would cause the electrodes to come off as a result of minor movements or perspiration of a patient and, on the contrary, too large a negative pressure in the suction cups could often cause subcutaneous bleeding in the chest wall of the patient. On the other hand, the tape method has such additional problems that it tends to cause skin redness due to the use of the adhesive tape and give uncomfortable bodily sensations to the patient when the adhesive tape is attached or detached.

To overcome the aforementioned problems, the inventor of the present invention previously proposed an EKG recording electrode holder in Japanese Registered Utility Model No. 1902495. This EKG recording electrode holder has a pair of front parts and a back part which are assembled to form a front-opening vest-like design with a zipper or other opening/closing device fitted to the front parts. The front parts of this electrode holder where electrodes are passed and maintained are of a mesh fabric made of stretchable fiber yarn.

The EKG recording electrode holder for electrocardiography of the aforementioned Utility Model is advantageous in that only if a patient puts it on in a manner of wearing a vest, it becomes possible to take an electrocardiogram with the electrodes held in the front parts of the electrode holder in close contact with the skin surface. This electrode holder, however, has a problem that it is time-consuming to make a patient of an emergency case on site put it on, for example, if it is difficult to change the position of the patient.

SUMMARY OF THE INVENTION

This invention is intended to provide a solution to the aforementioned problems of the prior art. Accordingly, it is an object of the invention to provide an EKG recording electrode device which can be easily and quickly fitted to a patient without giving uncomfortable bodily sensations to the patient even if it is difficult to change the position of the patient, making it possible to properly take an electrocardiogram.

According to a main feature of the invention, an EKG recording electrode device comprising, an electrode holder made of a sheet material having flexibility and a size suited for placing on an upper front part of a human body, and a plurality of electrodes attached to the electrode holder, each electrode including a contact portion having a curved surface on the side which comes into contact with a human skin.

In this construction, the electrode holder carrying the multiple electrodes can be fitted to the upper front part of the human body by just placing the electrode holder thereupon without the need to apply jelly for the electrodes or to attach the electrodes with adhesive tape. Since the contact pads attached to the electrodes are held in stable contact with the human skin surface in this condition, it is possible to correctly take an electrocardiogram.

Moreover, the standard 12-lead electrocardiogram can be taken easily and correctly, free from such problems as poor electrical contact of the electrodes due to the body shape or body hair of the patient or coming off of the electrodes from the human skin surface as a result of respiration or perspiration of the patient not only in ordinary diagnosis but also in emergency cases. Electrocardiographic waves recorded by an electrocardiograph may be transmitted to a critical medical care center, a hospital or a remote medical institution via a radio communications. This is advantageous in that a physician can recognize changes in the electrocardiogram of the patient on a real-time basis and give instructions back to the ambulance so that ambulance personnel can promptly take appropriate measures.

In one aspect of the invention, the electrode holder is formed into a shape which properly fits on the upper front part of the human body.

Since the electrode holder is correctly fitted on the upper front part of the human body by just placing the electrode holder thereupon in this construction, the contact pads of the electrodes can be held in stable contact with the human skin surface and it is possible to take the electrocardiogram correctly without causing the electrode holder to slip off the upper front part of the human body.

In another aspect of the invention, a pair of shoulder flaps which hang along the shoulders of the human body or a pair of side flaps which hang along the sides of the stomach of the human body are provided at upper left and right parts or at lower left and right parts of the electrode holder, respectively.

Since the flaps hanging along the shoulder tops and/or the sides of the stomach of the human body produce a pulling force acting symmetrically on the left and right sides in this construction, the electrode holder is kept from moving. Therefore, although the electrode holder is constructed to be fitted by just placing it on the upper front part of the human body, the electrode holder can be held in position in a stable fashion.

In a further aspect of the invention, joints made of a stretchable material are provided between the electrode holder and the individual flaps.

This alternative is advantageous in that it is possible to cause the flaps to properly hang along the left and right shoulder tops and/or along both sides of the stomach of the human body as the flaps can be easily bent at the respective joints when the EKG recording electrode device is in use, and the physical size of the electrode holder can be reduced by folding the flaps at the respective joints to the rear side when the EKG recording electrode device is not used.

These and other objects, features and advantages of the invention will become more apparent upon reading the following detailed description in conjunction with the accompanying drawings.

DETAILED DESCRIPTION OF THE PREFERRED EMBODIMENT OF THE INVENTION

Figure 1:
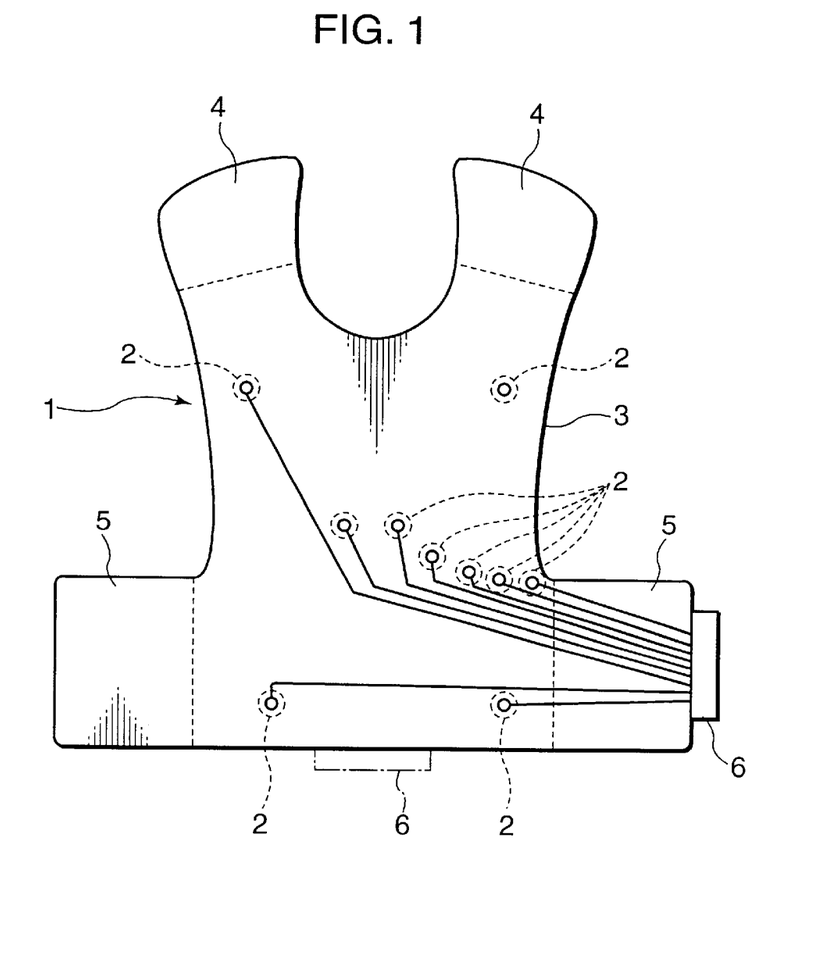
FIG. 1 is an explanatory diagram showing an EKG recording electrode device according to an embodiment of the present invention.

FIG. 1 is an explanatory diagram showing an EKG recording electrode device according to an embodiment of the present invention. This EKG recording electrode device comprises an electrode holder 1 formed generally into a sheet like shape using a sheet material 1a having flexibility, such as flexible synthetic resin like non-rigid vinyl chloride, flexible rubber or silicone rubber-coated fabric, a plurality of electrodes 2 fitted at positions which corresponds to ordinary potential measuring positions when the electrode holder 1 is fitted to an upper front part of a human body, and a connector 6 for connecting the electrode holder 1 to an unillustrated electrocardiograph.

Figure 2:
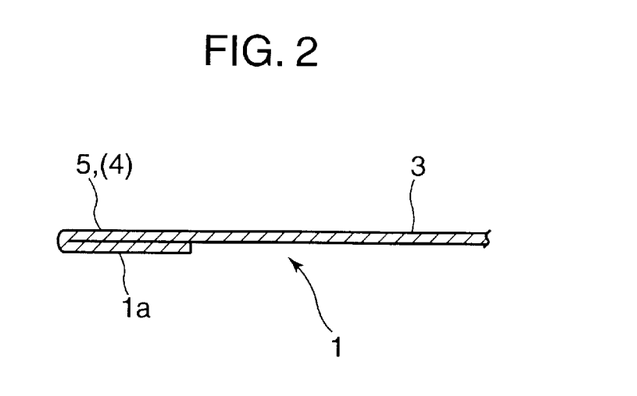
FIG. 2 is a cross-sectional diagram showing the structure of each flap of an electrode holder of the EKG recording electrode device.

The electrode holder 1 has a holder body 3 formed in a size appropriate to cover the upper front part of the human body, a pair of shoulder flaps 4 provided at upper left and right parts of the holder body 3, and a pair of side flaps 5 provided at lower left and right parts of the holder body 3. As shown in FIG. 2, the shoulder flaps 4 and the side flaps 5 have a double-layer structure made by folding back ends of the sheet material 1a extending from the holder body 3 to the rear side and bonding the folded parts.

Figure 3:
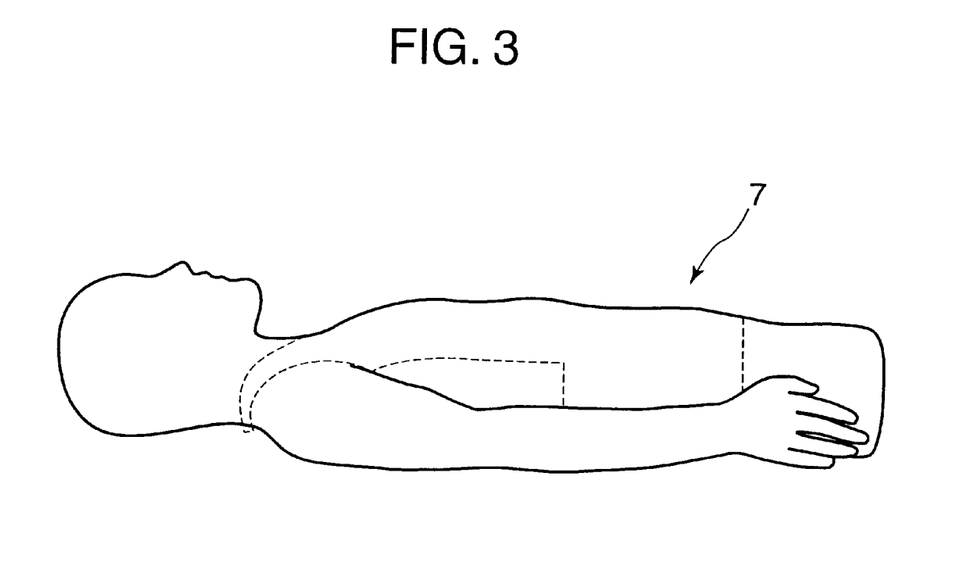
FIG. 3 is an explanatory diagram showing how the electrode holder is molded.

The electrode holder 1 is formed by means of a mold made from a master 7 as shown in FIG. 3, for example, which is produced by using a cast of the upper front part of the human body. In this molding operation, the electrode holder 1 is made such that it properly fits on the upper front part of the human body with the rear side of the electrode holder 1 shaped to form continuous curved surfaces including concave parts corresponding to the breasts, stomach and other swelling parts of the human body and convex parts corresponding to the pit of the stomach and other hollow parts of the human body.

Each of the electrodes 2 has a contact pad 8 made of copper, brass, stainless steel or carbon-fiber composite whose outer surface comes into contact with a human skin surface A is shaped to form a curved surface, such as a hemisphere, and a connector 10 to which a connecting wire harness 9 is connected. The contact pad 8 is fitted to the electrode holder 1 by bonding it to the rear side of the electrode holder 1, for instance, with the connector 10 passed through a hole made in the electrode holder 1. The individual connectors 10 are connected to the connecting wire harness 9 which is run along an outer surface of the electrode holder 1. In one varied form of the embodiment, the connecting wire harness 9 may be embedded in the sheet material 1a of the electrode holder 1.

Assuming that a patient has been carried into an ambulance, for example, the EKG recording electrode device of this embodiment can be mounted by just placing it on the upper front part of the patient. The EKG recording electrode device is used with the shoulder flaps 4 and the side flaps 5 hanging along the shoulder tops and the sides of the stomach of the patient, respectively.

An electrocardiogram of the patient is taken with the connector 6 of the electrode holder 1 connected to a connector of electrocardiograph which is mounted on the ambulance. Electrocardiographic waves recorded by the electrocardiograph may be transmitted to a critical medical care center, a hospital or a remote medical institution via a radio communications, enabling a physician to recognize changes in the electrocardiogram on a real-time basis and give instructions back to the ambulance so that ambulance personnel can promptly take appropriate measures.

Figure 4:
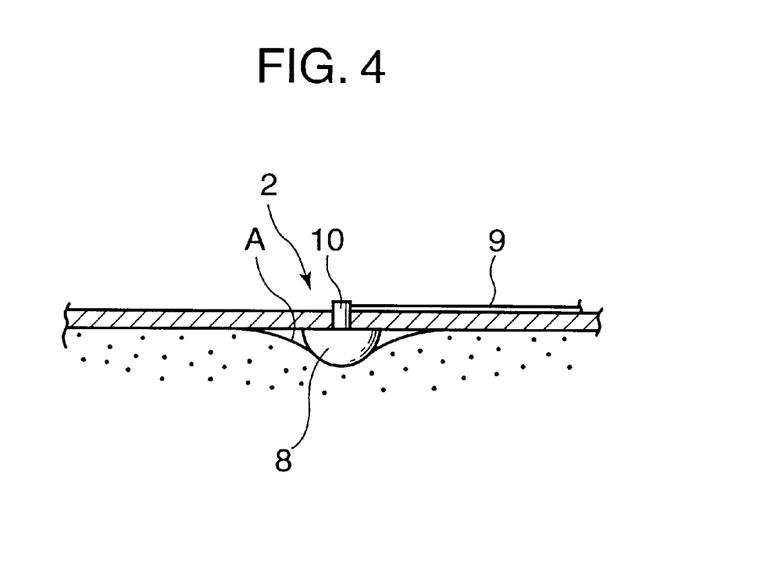
FIG. 4 is an explanatory diagram showing how an electrode is held in contact with a human body.
Figure 5:
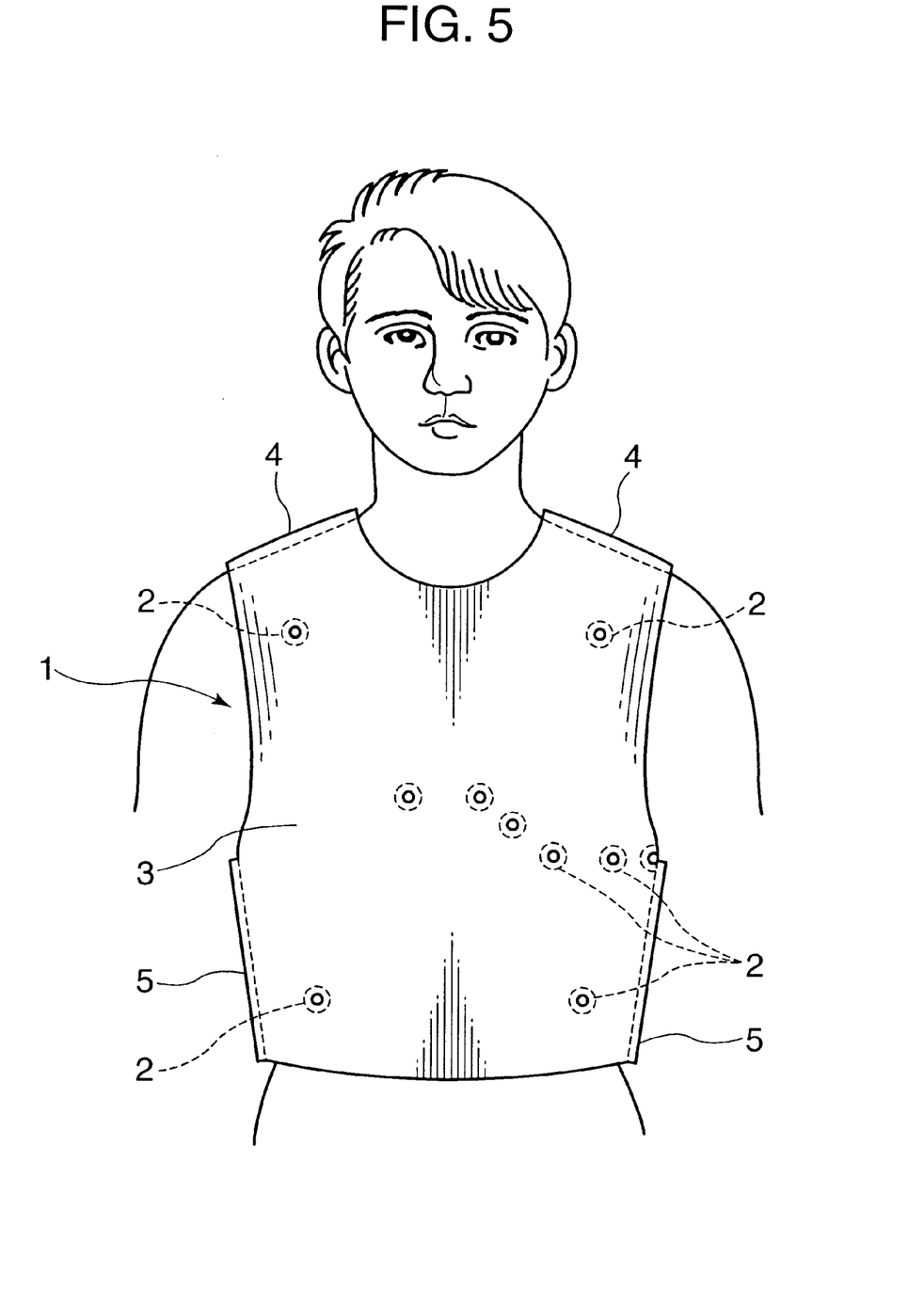
FIG. 5 is an explanatory diagram showing how the EKG recording electrode device of the invention fitted to the human body.

As so far described, in the EKG recording electrode device comprising the electrode holder 1 formed of the flexible sheet material 1a of a proper size to be placed over the upper front part of the human body and a plurality of electrodes 2 attached to the electrode holder 1, each of the electrodes 2 is fitted with the contact pad 8, whose outer surface comes into contact with the human skin surface A, having a curved surface. This curving surface of the contact pad 8 makes it possible to come into contact with the human skin surface A firmly even if the human skin surface A is recessed where any of the electrodes 2 is placed as shown in FIG. 4 In addition, the electrode holder 1 of the present invention can be mounted on the upper front part of a patient properly because the electrode holder 1 is easily deformed to fit the shape of the upper body of a patient.

Thus, it is possible to easily and securely hold the contact pads 8 of the electrodes 2 in contact with the human skin surface A without the need to apply jelly for the electrodes 2 or to attach the electrodes 2 with adhesive tape. Even in a case of being difficult to change the position of the patient at an emergency site, for instance, it is possible to quickly and precisely take an electrocardiogram of the patient. Moreover, the standard 12-lead electrocardiogram can be taken correctly, free from such problems as poor electrical contact of the electrodes 2 due to the body shape or body hair of the patient or coming off of the electrodes 2 from the skin surface A as a result of respiration or perspiration of the patient.

Figure 6:
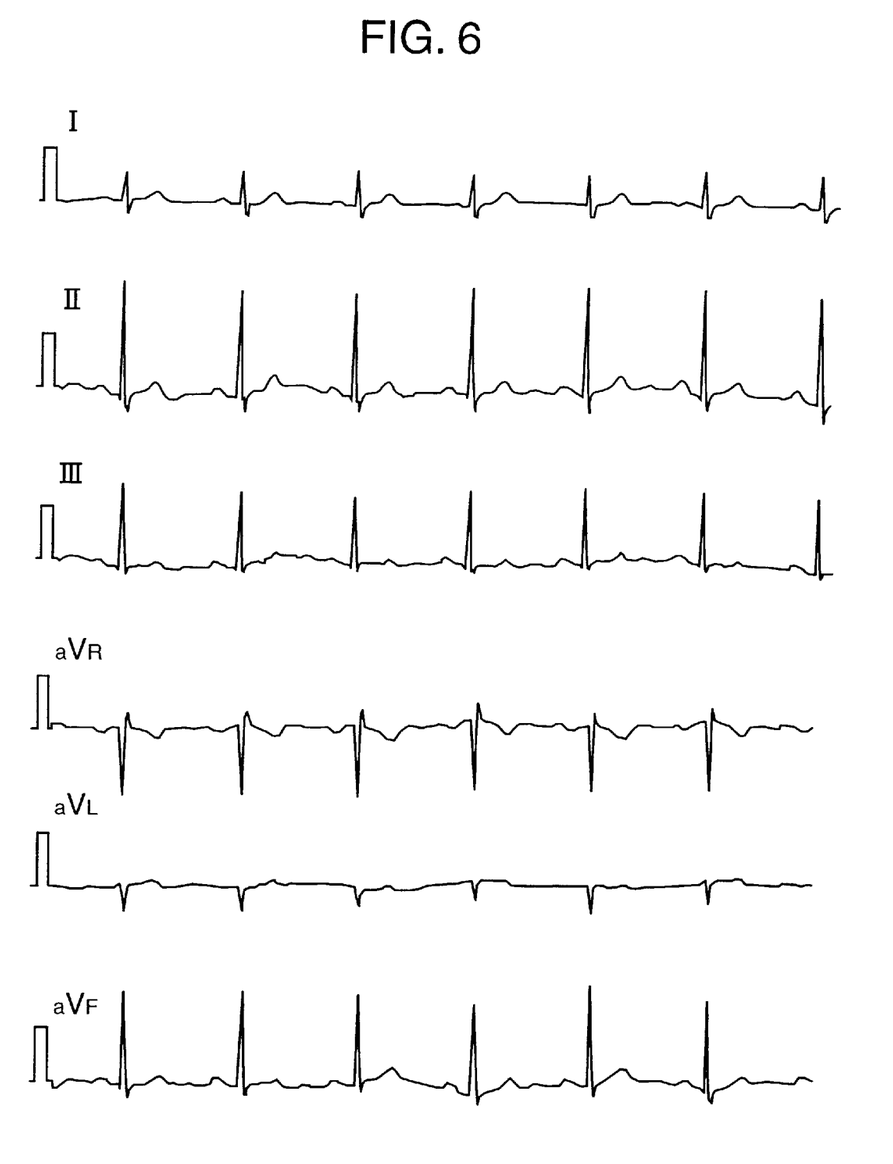
FIG. 6 is a chart showing standard limb leads (I, II<III, aVR, aVL, aVF)
Figure 7:
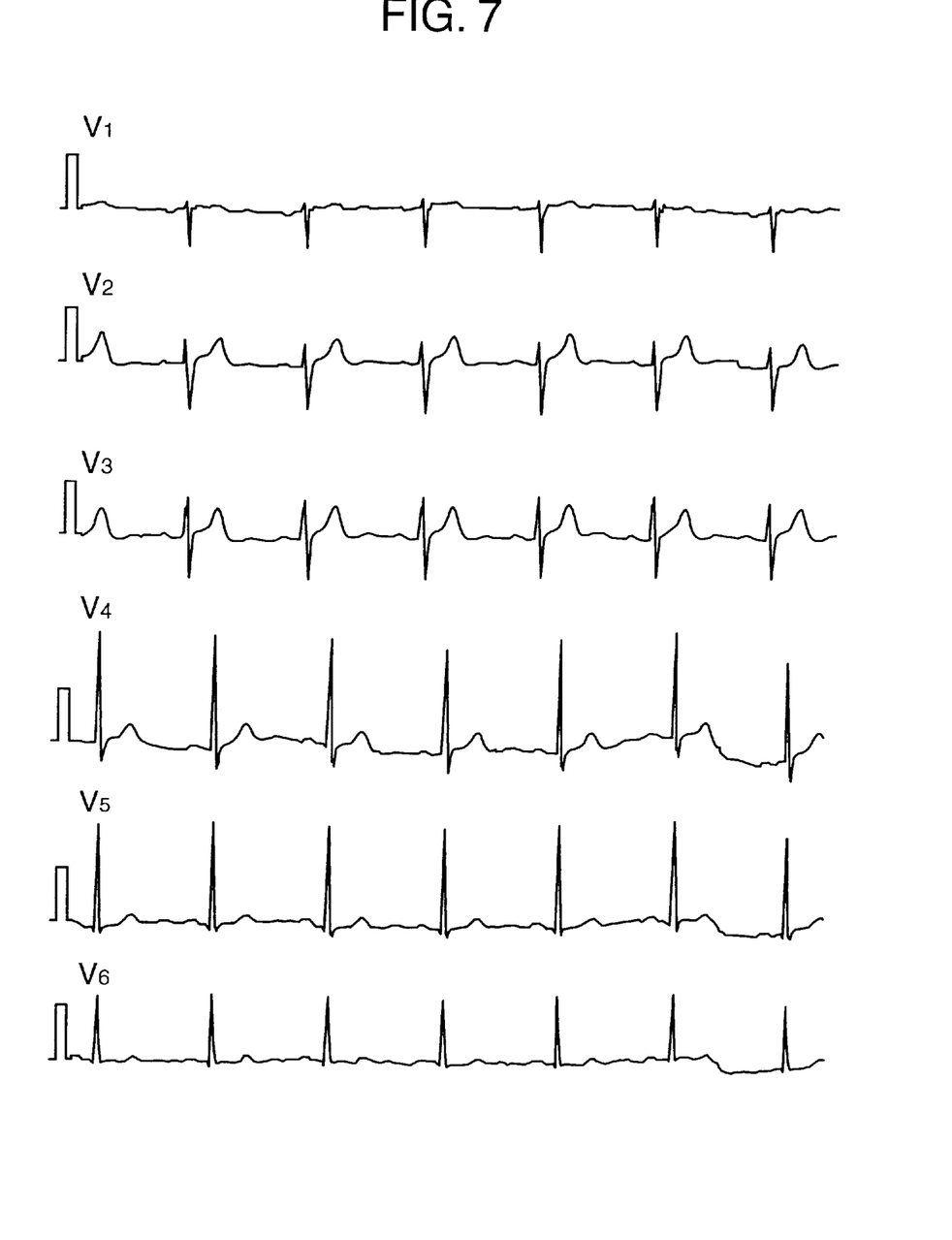
FIG. 7 is a chart showing unipolar chest leads (V1–V6)

The present inventor conducted a test using the EKG recording electrode device of this invention and obtained electrocardiograms including standard limb leads (I, II<III, aVR, aVL, aVF) and unipolar chest leads (V1–V6), proving the ability of this EKG recording electrode device to produce the standard 12-lead electrocardiogram which is comparable to what is obtained with conventional EKG recording electrode devices. The test also proved that the EKG recording electrode device of the present invention would not cause the problems of coming off of the electrodes 2 or poor contact.

Figure 8:
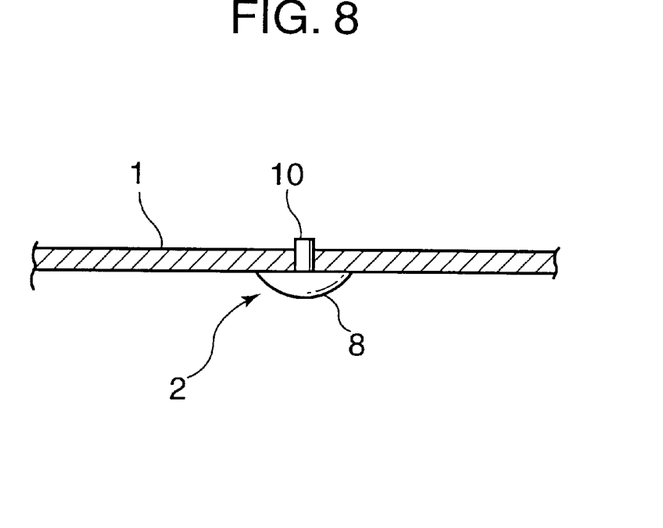
FIG. 8 is an explanatory diagram showing a variation of an electrode in the present invention.

In particular, when the contact pads 8 of the electrodes 2 are formed into a hemispherical shape as in the present embodiment, there are produced such advantageous effects that the electrode holder 1 can adjust itself to various inclinations of the human skin surface A and the contact pads 8 can be securely held in contact with the skin surface A because the contact surfaces of the contact pads 8 have a curved shape. It is to be noted, however, that the structure of the contact pads 8 is not limited to the hemispherical shape but may be of a bowl like shape as shown in FIG. 8.

Also, when the electrode holder 1 is formed into a shape which properly fits on to the upper front part of the human body in the EKG recording electrode device comprising the electrode holder 1 to be placed over the upper front part of the human body and a plurality of electrodes 2 attached to the electrode holder 1, it is possible to easily mount the electrode holder 1 by just placing it on the upper front part of the human body and to effectively prevents the electrode holder 1 from slipping off the upper front part of the human body. As a consequence, the contact pads 8 of the electrodes 2 can be held in position in stable contact with the human skin surface A.

For practical application of the invention, it is preferable to prepare several types of EKG recording electrode devices having electrode holders 1 of different sizes and shapes to allow the choice of the EKG recording electrode devices depending on the physical makeup of individual patients. More specifically, it would be desirable to prepare EKG recording electrode devices having electrode holders 1 for male and female patients, both in large, medium and small sizes, for example.

As stated above, the electrode holder 1 of the EKG recording electrode device of the present embodiment is provided with the shoulder flaps 4 and the side flaps 5 at the upper left and right parts and at the lower left and right parts of the holder body 3 which hang along the shoulder tops and along the sides of the stomach of the patient, respectively. These flaps 4, 5 serve as restraints which prevent the electrode holder 1 from slipping off the human body during electrocardiographic testing. This structure of the electrode holder 1 makes it possible to mount the EKG recording electrode device in a more stable fashion.

More specifically, with the left and right shoulder flaps 4 hanging along the shoulder tops of the human body, a pulling force acting symmetrically on the left and right sides of the neck is produced, and with the left and right side flaps 5 hanging along the sides of the stomach of the human body, a pulling force acting symmetrically on the left and right sides is produced at the lower left and right parts of the holder body 3. Consequently, the electrode holder 1 can be fitted on the patient body in a stable fashion with a reduced risk of slipping off the upper front part of the human body.

As previously stated, the shoulder flaps 4 and the side flaps 5 have the double-layer structure produced by folding back the ends of the sheet material 1a extending from the holder body 3 to the rear side. This double-layer structure of the shoulder flaps 4 and the side flaps 5 gives them extra weights. The present embodiment of the invention is also advantageous in that it is possible to improve the function of the flaps 4, 5 as the restraints with such a simple design and thereby prevent the electrode holder 1 from slipping off the human body even more securely.

Although the foregoing discussion has dealt with the preferred embodiment of the invention in which the electrode holder 1 is provided with the shoulder flaps 4 and the side flaps 5 at the upper left and right parts and at the lower left and right parts of the holder body 3, respectively, either the shoulder flaps 4 or the side flaps 5, or all of them, may be eliminated in an alternative form of the invention.

Also, instead of adopting the aforementioned double-layer structure, the weights of the flaps 4, 5 may be increased by making upper left and right parts and lower left and right parts of the sheet material 1a thicker than the holder body 3, or by attaching weights to the individual flaps 4, 5. In another alternative form of the invention, the flaps 4, 5 may be formed to specific lengths such that they can be wound to the back of the human body when fitting the electrode holder 1.

Figure 9:
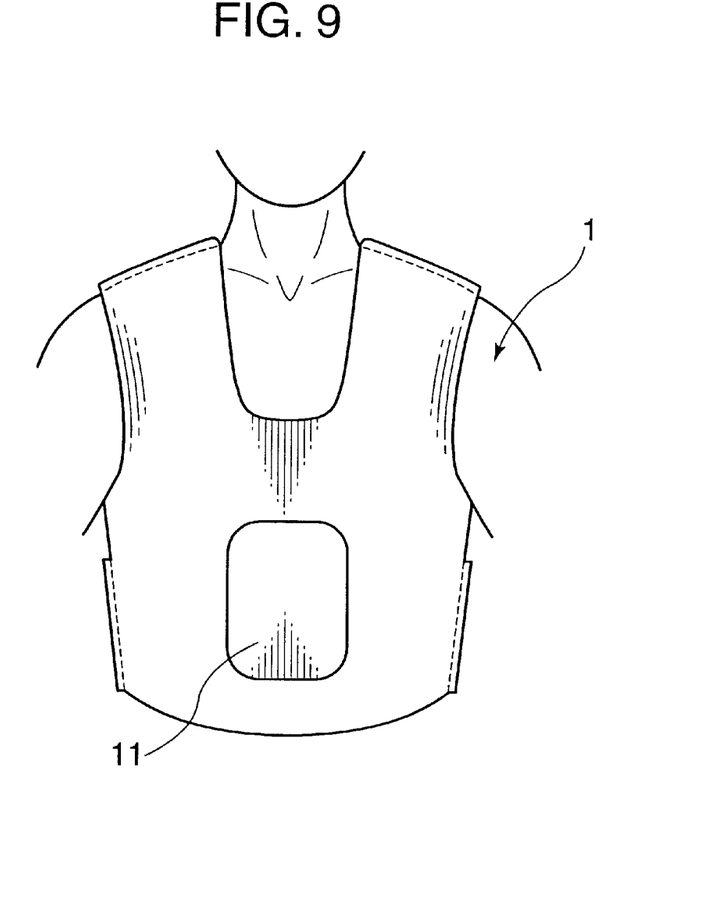
FIG. 9 is an explanatory diagram showing an EKG recording electrode device according to another variation of the embodiment.
Figure 10:
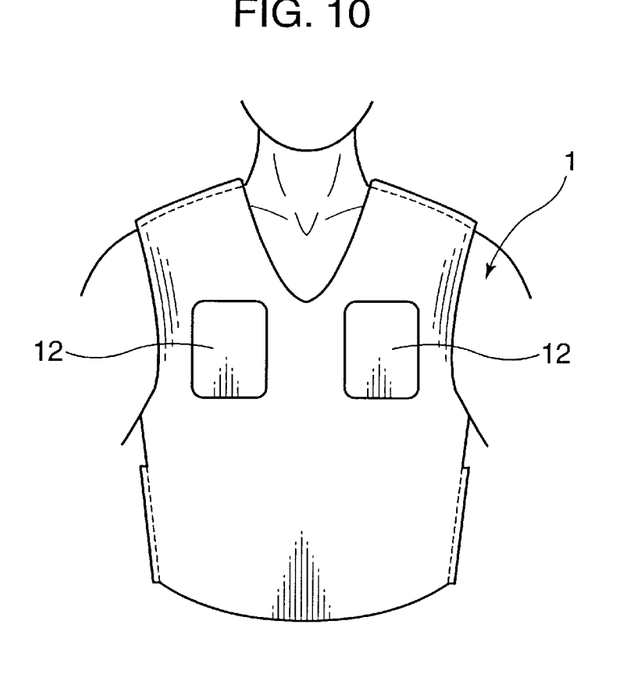
FIG. 10 is an explanatory diagram showing an EKG recording electrode device according to still another variation of the embodiment.

Furthermore, one or more holes 11, 12 may be made in the electrode holder 1 where the electrodes 2 are not present for reducing the weight of the electrode holder 1 as shown in FIGS. 9 and 10. This structure is advantageous in that it helps to alleviate stress on the patient due to the reduced weight of the electrode holder 1 and it makes the patient more comfortable when putting on the electrode holder 1 with improved passage of air.

Figure 11:
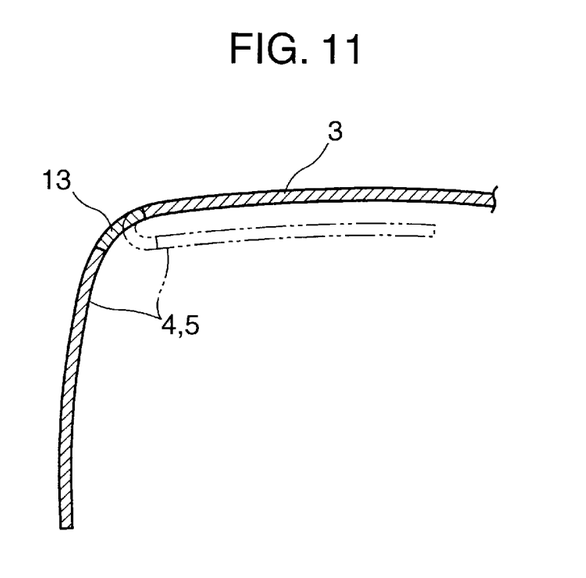
FIG. 11 is an explanatory diagram showing an EKG recording electrode device according to yet another variation of the embodiment.

In yet another alternative form of the invention, there may be provided a joint 13 made of a stretchable material like a mesh fabric which is made of stretchable fiber yarn such as spandex between the holder body 3 and each of the flaps 4, 5 as shown in FIG. 11. This alternative is advantageous in that it is possible to cause the flaps 4, 5 to properly hang along the left and right shoulder tops and along both sides of the stomach of the human body as the flaps 4, 5 can be easily bent at the respective joints 13 when the EKG recording electrode device is in use, and the physical size of the electrode holder 1 can be reduced by folding the flaps 4, 5 at the respective joints 13 to the rear side when the EKG recording electrode device is not used.

Another form of the invention is described along with FIGS. 12A–12D, and 13. In this form, a pair of shoulder flaps 4A, 4A are detachably attached to a holder body 3A at positions corresponding to left and right shoulder portions of a human body when the holder body 3A is placed over the upper front part of a human body. In addition, a pair of side flaps 5A and 5B are also detachably attached to the holder body 3A at positions corresponding to left and right sides of a human body when the holder body 3A is placed over the upper front part of a human body. As the holder body 3A is symmetrical in shape, we would like to only describe the right half side of the structure.

Figure 12A:
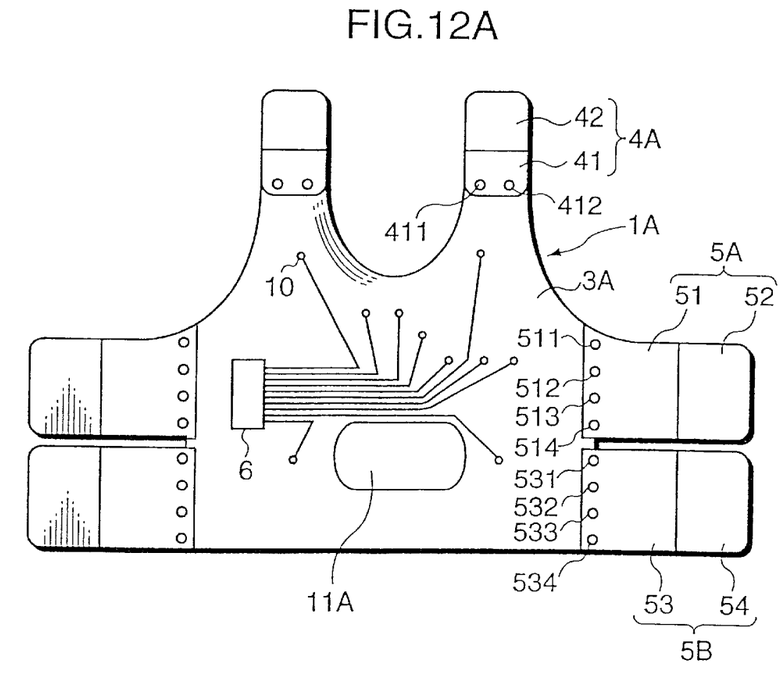
FIG. 12A shows the front side of an EKG recording electrode device when it is attached to the human body.
Figure 12B:
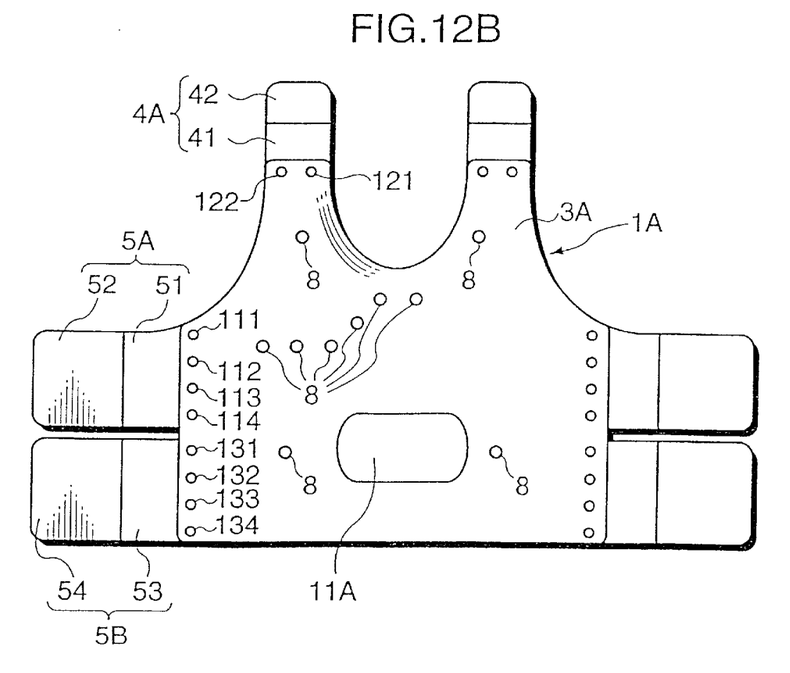
FIG. 12B shows the backside view of FIG. 12A.

Each of the shoulder flaps 4A is formed by two parts, namely a first part 41 and a second part 42, that are securely fixed to each other by heating process. The first part 41 is made of a material such as a rubber, but not limited thereto, having a higher elasticity as well as a flexibility. The second part 42 is made of a material such as vinyl chloride, but not limited thereto, having a great flexibility. On one end of the first part 41, two permanent magnets 411, 412 (referred to as a first set of magnets) are fixed as shown in FIG. 12A. At the positions corresponding to those two magnets 411, 412, two permanent magnets 121, 122 (referred to as a second set of magnets) are fixed to the holder body 3A as shown in FIG. 12B.

Figure 12C:
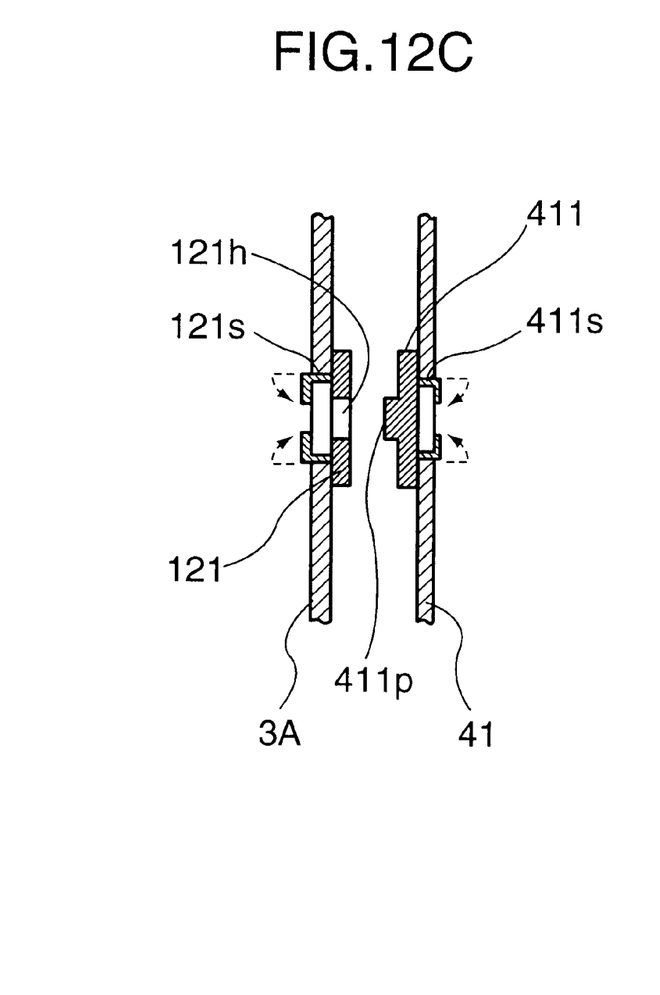
FIG. 12C is an enlarged side view showing a magnet structure attached to the holder body and a magnet structure attached to a shoulder flap.
Figure 12D:
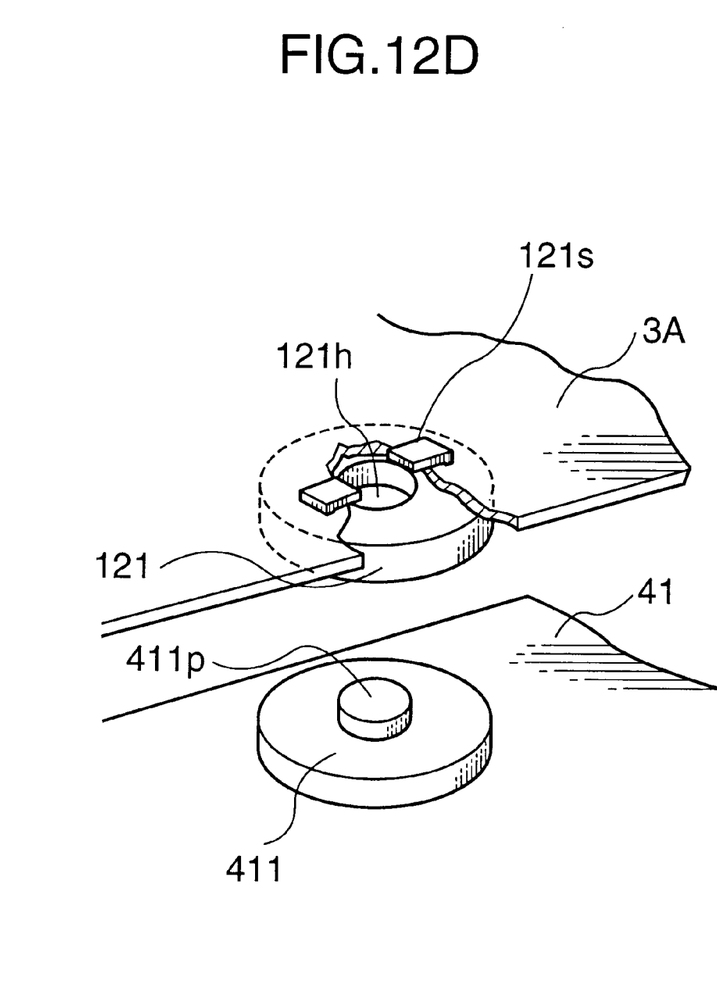
FIG. 12D is an enlarged three-dimensional view showing a magnet structure attached to the holder body and a magnet structure attached a shoulder flap.

FIG. 12C is an enlarged side view showing a magnet structure attached to the holder body and a magnet structure attached to a shoulder flap. FIG. 12D is an enlarged three-dimensional view showing a magnet structure attached to the holder body and a magnet structure attached to a shoulder flap. A magnet 121 is identical to each of magnets 122, 111, 112, 113, 114, 131, 132, 133, 134 and a magnet 411 is identical to each of magnets 412, 511, 512, 513, 514, 531, 532, 533, 534. Therefore, only magnets 121, 411 are described as representatives of other magnets hereinafter. The magnet 411 has a projected portion 411p and the magnet 121 has a concave portion 121h. A magnet 121 has a pair of stoppers 121s which penetrate the holder body 3A and a pair of stoppers 121s are folded back along the holder body 3A to fix the magnet 121 onto the holder body 3A. A magnet 411 has a pair of stoppers 411s which penetrate the shoulder flap 41 and a pair of stoppers 411s are folded back along the flap 41 to fix the magnet 411 onto the flap 41. The magnet 411 and the magnets 121 are attached in such a way that a projected portion 411p of the magnet 411 is fitted into the concave portion 121h of magnet 121. It should be noted that the magnets 411 and the magnet 121 are interchangeable with respect to the holder body 3A and the flap 4A. Therefore, the magnets 411 may have the concave portion which may be fixed to the corresponding projected portion of the magnet 121.

It also should be noted, however, those elements securely fixing the shoulder flap 4A onto the holder body 3A need not be in the form of the magnet as shown and described in this specification. It should be considered to be in a matter of design choice so long as the shoulder flap 4A is easily and securely detachably attached to the holder body 3A.

A side flap 5A has a very similar construction to the shoulder flap 4A. Similarly, the side flap 5A is formed by two parts, namely a first part 51 and a second part 52, that are securely fixed to each other by heating process. There are four magnets, 511, 512, 513, 514 fixed onto the first part 51 of the side flap 5A. The magnets 511, 512, 513, 514 are detachably attached to corresponding magnets 111, 112, 113, 114 provided on the side portion of the holder body 3A. It should be noted, however, the number of magnets provided in the side flap 5A or the holder body 3A is no way limited to this particular embodiment.

Underneath the side flap 5A in FIGS. 12A, 12B, a very similar side flap 5B is provided. Similarly, two parts, namely first part 53 and a second part 54 are bonded together by heating process and four magnets 531, 532, 533, 534 are fixed onto the first part 53 of the side flap 5B. The magnets 531, 532, 533, 534 are detachably attached to the corresponding magnets 131, 132, 133, 134 on the side of the holder body 3A.

The structure of the side flap 5B can be exactly the same as the structure of the side flap 5A. In other words, it may be possible to use the identical member for both side flaps 5A and 5B. In the embodiment shown in FIGS. 12A, 12B, the identical side flap 5A (5B) is used; thus there are four identical side flaps 5A, 5A, 5B, 5B, detachably attached to the holder body 3A. Similar to the shoulder flap 4A, the first part 51 (53) of side flap 5A (5B) is made of a material such as a rubber, but not limited thereto, having a higher elasticity as well as a flexibility. The second part 52 (54) of the side flap 5A (5B) is made of a material such as vinyl chloride, but not limited thereto, having a great flexibility.

Because of the materials used for each flap, the flap can be flexibly bent and fit along a non-straight curved surface of the human body. In addition, the elasticity of the first part enables to pull the holder body 3A so that any wrinkle, if exists on the surface of the holder body 3A, can be corrected.

Because of the aforementioned detachable structure of the shoulder flap (4A) and the side flap 5A (5B), several kinds of the shoulder flaps or side flaps having different sizes and lengths can be attachable to the same holder body 3A. Accordingly, the same holder body 3A can be used for people who have different configurations in body size by changing the shoulder flaps or side flaps.

Figure 13:
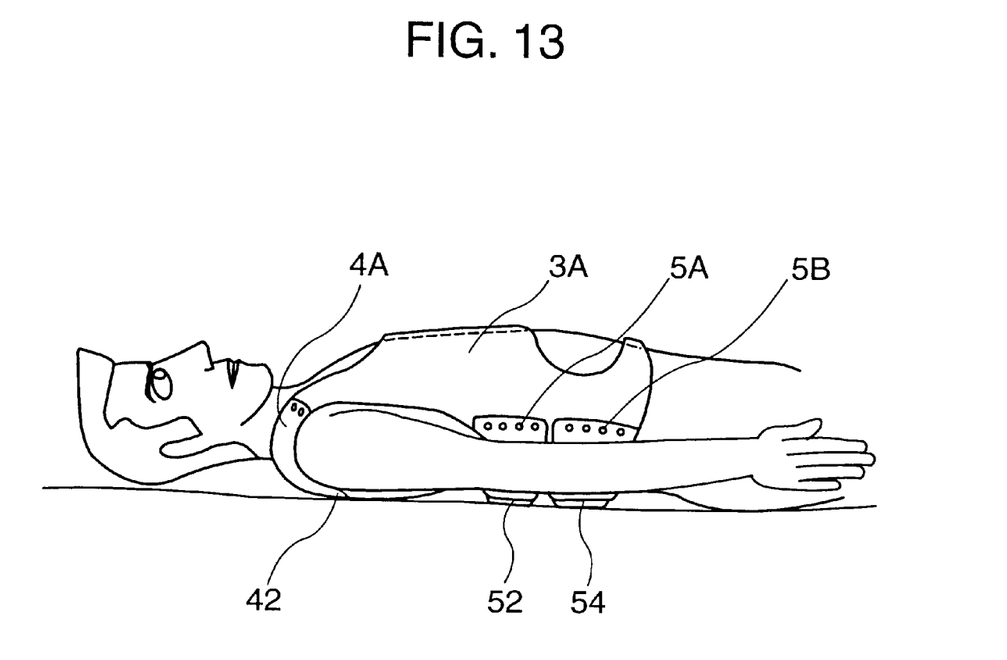
FIG. 13 is an explanatory diagram showing how the EKG recording electrode device of FIG. 12 fitted to the human body.

With the aforementioned structure, when the need arises, first of all, the holder body 3A is placed over the upper front part of the human body assuming a person is already lie down over a bed. Thereafter, both the shoulder flaps 4A and the side flaps 5A, 5B are attached to the holder body 3A by coinciding the magnet locations of flaps 4A, 5A, 5B with the magnet locations of the holder body 3A. Thus, no screwing operation is needed to fasten the flaps 4A, 5A, 5B, onto the holder body 3A. Then, the second part 42 of the shoulder flap 4A is stretched downward by an adequate amount to be slid down under the upper shoulder of the human body. At the same time, the second part 52 (54) of the side flap 5A (5B) is stretched downward by an adequate amount to be slid down under the side of the human body. Since the second parts of shoulder flaps 4A and the second parts of side flaps 5A (5B) can be held between the human body and the bed as shown in FIG. 13, the holder body 3A is adequately fitted onto the upper front body so that contact pads 8 are prevented from being spaced apart from the skin surface A.

Note that the length of the shoulder flap 4A and the length of the side flap 5A (5B) are so set as to be sufficiently enough to be placed underneath the human body lying down on bed. It should also be noted that the size of the human body varies not only in accordance with age but also with gender, race, or bone structures. Thus, there required to prepare in advance several kinds of flaps having different sizes as well as the holder body 3A to cope with the a various size of human bodies.

It should also be noted that the number of flaps on each side of the holder body 3A is not limited to the aforementioned example that is two on each side. Moreover, an opening 11A is formed in the holder body 3A at a position corresponding to a navel, but not limited thereto, when the holder body 3A is placed over the upper front part of the human body. The size and shape of the opening 11A is considered to be a matter of design choice.

The invention has thus far been described with reference to the embodiment in which the connector 6 is provided in one of the left and right side flaps 5, however, the connector 6 may be provided at a lower central part of the holder body 3 as shown by an imaginary line in FIG. 1. This structure makes it possible to properly connect the EKG recording electrode device to the electrocardiograph regardless of whether the electrocardiograph is located to the left or right of the electrode holder 1.

This application is based on Japanese application serial No. H11-231548 filed in Japan on Aug. 18, 1999, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An EKG recording electrode device comprising:
    an electrode holder made of a sheet material having flexibility and a size suited for placing on an upper front part of a human body;
    the electrode holder including:
        a main portion;
        a pair of shoulder flap portions, provided at the upper left and right parts of the electrode holder; and
        a pair of side flap portions provided at lower left and right parts of the electrode holder, the shoulder flap portions and the side flap portions adapted for hanging along the shoulder tops and along the sides of the stomach of the human body, respectively when the EKG recording electrode device is in use; and
    a plurality of electrodes attached to the electrode holder, each electrode including a contact portion having a curved surface on the side which comes into contact with a human skin, wherein the electrode holder is formed into a shape which fits the upper front part of the human body.

2. The EKG recording electrode device according to claim 1, wherein the electrode holder further including:
    joint portions made of a stretchable material provided between the main portion and the individual flap portions of the electrode holder.

3. The EKG recording electrode device according to claim 1, wherein the main portion is formed with a hole for reducing the weight of the electrode holder.

4. The EKG recording electrode device according to claim 1, wherein the main portion is formed with two holes at positions corresponding to left and right portions of chest of the human body when in use.

5. The EKG recording electrode device according to claim 1, wherein the main portion is formed with a hole at position corresponding to a stomach of the human body when in use.

6. An EKG recording electrode device comprising:
    an electrode holder made of a continuous sheet material having a flexibility and a size limited for being placed only over an upper front part of a human body;
    the electrode holder including:
        a main portion,
        a pair of shoulder flap portions, and
        a pair of side flap portions, and
        all said portions being made of a single sheet material; and
    a plurality of electrodes attached to the electrode holder, each electrode including a contact portion adapted for being in contact with a human skin when in use, wherein the shoulder flap portions each has a thickness substantially twice a thickness of the main portion.

7. The EKG recording electrode device according to claim 6, wherein the side flap portions each has a thickness substantially equal to the shoulder flap portion.

8. A method of using an EKG recording electrode device comprising an electrode holder made of a sheet material including a main portion, to which a plurality of electrodes are attached, a pair of shoulder flap portions, and a pair of side flap portions comprising the steps of:
    placing the main portion of the electrode holder over an upper front half part of a human body such that the electrodes are in contact with the human skin;
    hanging the pair of shoulder flap portions along top portions of shoulder of the human body; and
    hanging the pair of side flap portions along sides of the stomach of the human body.

9. The method according to claim 8, wherein the EKG recording electrode device further comprises a connector attached to the main portion for transmitting signals received from the electrodes to an electrocardiograph, further comprising the step of connecting the connector to a connector of the electrocardiograph.

10. An EKG recording electrode device comprising:
    an electrode holder made of a sheet material having a flexibility and a size limited for being placed only over an upper front part of a human body;
    a pair shoulder flap members, each of which is detachably attached to the electrode holder at positions corresponding to left and right shoulder when in use;
    a pair of side flap members, each of which is detachably attached to the electrode holder at positions corresponding to left and right sides of a human body when in use;
    a plurality of electrodes attached to the electrode holder; each electrode includes a contact portion which is adapted for being in contact with a human skin when in use.

11. An EKG recording electrode device according to claim 10, wherein at least one shoulder flap member of the pair of shoulder flap members includes a first part and a second part.

12. An EKG recording electrode device according to claim 11, wherein the first part is provided with a first set of magnets and the corresponding portion of the electrode holder is provided with a second set of magnets and the first set of magnets and the second set of magnets are attracted to each other to securely hold the at least one shoulder flap member of the pair of shoulder flap members to the electrode holder.

13. An EKG recording electrode device according to claim 11, wherein the second part is fixed to one end of the first part opposite to the end where the first set of magnets are provided.

14. An EKG recording electrode device according to claim 13, wherein the at least one shoulder flap member of the pair of shoulder flap members has a length sufficient enough such that the second pat is to be held under a back of a human body when in use.

15. An EKG recording electrode device according to claim 11, wherein the first part is made of an elastic material and the second part is made of a flexible material.

16. An EKG recording electrode device according to claim 15, wherein at least one side flap member of the pair of side flap members includes a first part and a second part.

17. An EKG recording electrode device according to claim 16, wherein the first part is provided with a first set of magnets and the corresponding portion of the electrode holder is provided with a second set of magnets and the first set of magnets and the second set of magnets are attracted to each other to securely hold the at least one side flap member of the pair of side flap members to the electrode holder.

18. An EKG recording electrode device according to claim 17, wherein the second part is attached to one end of the first part opposite to the end where the first set of magnets are provided.

19. An EKG recording electrode device according to claim 18, wherein the at least one side flap member of the pair of side flap members has a length sufficient enough such that the second part is to be held under a back of a human body when in use.

20. An EKG recording electrode device according to claim 16, wherein the first part is made of an elastic material and the second part is made of a flexible material.

\* \* \* \* \*